(12) United States Patent
Dubois et al.

(10) Patent No.: US 7,784,348 B2
(45) Date of Patent: Aug. 31, 2010

(54) ARTICULATED ROBOT FOR LASER ULTRASONIC INSPECTION

(75) Inventors: Marc Dubois, Keller, TX (US); Thomas E. Drake, Jr., Fort Worth, TX (US); Kenneth Yawn, Weatherford, TX (US); Mark Osterkamp, Weatherford, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 395 days.

(21) Appl. No.: 11/709,342

(22) Filed: Feb. 21, 2007

(65) Prior Publication Data

US 2009/0010285 A1 Jan. 8, 2009

Related U.S. Application Data

(60) Provisional application No. 60/871,680, filed on Dec. 22, 2006.

(51) Int. Cl.
*G01N 29/06* (2006.01)
*G01N 29/26* (2006.01)

(52) U.S. Cl. .............................. 73/621; 73/620; 73/643

(58) Field of Classification Search .................. 73/643, 73/621, 620, 655, 634
See application file for complete search history.

(56) References Cited

U.S. PATENT DOCUMENTS

| | | | | |
|---|---|---|---|---|
| 4,338,822 | A  * | 7/1982 | Yamaguchi et al. | 73/643 |
| 6,378,387 | B1 * | 4/2002 | Froom | 73/865.8 |
| 6,571,633 | B1 * | 6/2003 | Drake, Jr. | 73/621 |
| 6,633,384 | B1 * | 10/2003 | Drake et al. | 356/432 |
| 6,643,002 | B2 * | 11/2003 | Drake, Jr. | 356/72 |
| 6,684,701 | B2 * | 2/2004 | Dubois et al. | 73/579 |
| 6,907,799 | B2 * | 6/2005 | Jacobsen et al. | 73/865.8 |
| 7,337,651 | B2 * | 3/2008 | Shankarappa et al. | 73/1.79 |
| 2004/0027578 | A1 * | 2/2004 | Drake et al. | 356/502 |
| 2004/0036042 | A1 * | 2/2004 | Drake, Jr. | 250/559.3 |

(Continued)

FOREIGN PATENT DOCUMENTS

| | | |
|---|---|---|
| WO | 00/00783 A1 | 1/2000 |
| WO | 02/06848 A2 | 1/2002 |
| WO | 02/18958 A2 | 3/2002 |

OTHER PUBLICATIONS

FANUC robotics, R-2000iA Series: http://www.fanucrobotics.com/file_repository/fanucmain/R-2000iA%20Series.pdf, available Oct. 10, 2005, 4 pages.*

(Continued)

*Primary Examiner*—Hezron Williams
*Assistant Examiner*—Rose M Miller
(74) *Attorney, Agent, or Firm*—Bracewell & Giuliani LLP

(57) ABSTRACT

An ultrasonic non-destructive evaluation (NDE) system operable to inspect target materials is provided. This ultrasonic NDE system includes an articulated robot, an ultrasound inspection head, a processing module, and a control module. The ultrasound inspection head couples to or mounts on the articulated robot. The ultrasound inspection head is operable to deliver a generation laser beam, a detection laser beam, and collect phase modulated light scattered by the target materials. The processing module processes the phase modulated light and produces information about the internal structure of the target materials. The control module directs the articulated robot to position the ultrasound inspection head according to a pre-determined scan plan.

17 Claims, 9 Drawing Sheets

U.S. PATENT DOCUMENTS

2004/0154402 A1    8/2004   Drake, Jr.
2005/0120803 A1    6/2005   Sokol et al.
2007/0006658 A1*   1/2007   Kennedy et al. ............. 73/622
2008/0291963 A1*   11/2008   Deaton et al. ................ 372/69

OTHER PUBLICATIONS

ABB IRB 6600: htttp://www.abb.co.in/global/inabb/inabb506.nsf/0/579e92967cad8bd16525703b00306b3e/$file/Robotics+IRB6600.pdf; available Oct. 10, 2005, 2 pages.*

* cited by examiner

ARTICULATED ROBOT FOR LASER ULTRASONIC INSPECTION

RELATED APPLICATIONS

This application claims priority to and incorporates by reference in its entirety for all purposes U.S. Provisional Application No. 60/871,680 filed on 22 Dec. 2006 entitled "ARTICULATED ROBOT FOR LASER ULTRASONIC INSPECTION" to Thomas E. Drake.

This application incorporates by reference in its entirety for all purposes U.S. Pat. No. 6,633,384, filed Jun. 30, 1999 which claimed the benefit of U.S. Provisional Application No. 60/091,240 filed on 30 Jun. 1998 and which is assigned to the assignee of the present application.

This application incorporates by reference in its entirety for all purposes U.S. Pat. No 6,122,060, filed Sep. 19, 2000 which claimed the benefit of U.S. Provisional Application No. 60/091,229 filed on 30 Jun. 1998 entitled "METHOD AND APPARATUS FOR DETECTING ULTRASONIC SURFACE DISPLACEMENTS USING POST-COLLECTION OPTICAL AMPLIFICATION" to Thomas E. Drake and which is assigned to the assignee of the present application.

This application incorporates by reference in its entirety for all purposes U.S. patent application Ser. No. 10/753,208 filed on 7 Jan. 2004 and entitled "REMOTE LASER BEAM DELIVERY SYSTEM AND METHOD FOR USE WITH A ROBOTIC POSITIONING SYSTEM FOR ULTRASONIC TESTING PURPOSES" to Thomas E. Drake.

This application incorporates by reference in its entirety U.S. patent application Ser. No. 10/634,342 filed on 12 Feb. 2004 and entitled "METHOD AND APPARATUS FOR ULTRASONIC LASER TESTING" to Thomas E. Drake.

This application incorporates by reference in its entirety U.S. patent application Ser. No. 11/458,377, entitled "FIBER LASER FOR ULTRASONIC TESTING." filed on Jul. 18, 2006 for all purposes.

This application incorporates by reference in its entirety U.S. patent application No. 11/524,046, entitled "Fiber-Based Mid-Infrared Generation Laser for Laser Ultrasound Inspection" filed on Sep. 20, 2006 for all purposes.

This application incorporates by reference in its entirety for all purposes U.S. Pat. No. 6,176,135 issued Jan. 23, 2001 and entitled "SYSTEM AND METHOD FOR LASER ULTRASONIC FREQUENCY CONTROL USING OPTIMAL WAVELENGTH TUNING."

This application incorporates by reference in its entirety for all purposes U.S. Pat. No. 6,335,943 issued Jan. 1, 2002 and entitled "SYSTEM AND METHOD FOR ULTRASONIC LASER TESTING USING A LASER SOURCE TO GENERATE ULTRASOUND HAVING A TUNABLE WAVELENGTH."

TECHNICAL FIELD OF THE INVENTION

The present invention relates generally to non-destructive evaluation (NDE), and more particularly, to the performance of laser ultrasonic NDE of materials from a robotic platform.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. This assessment detects inclusions, delaminations and porosities. Conventional NDE methods are slow, labor-intensive, and costly. As a result, testing procedures adversely increase the manufacturing costs associated with composite structures.

Various methods and apparatuses have been proposed to assess the structural integrity of composite structures. One solution uses an ultrasonic source to generate ultrasonic surface displacements in a work piece which are then measured and analyzed. Often, the external source of ultrasound is a pulsed generation laser beam directed at the target. Laser light from a separate detection laser is scattered by ultrasonic surface displacements at the work piece. Then collection optics collect the scattered laser energy. The collection optics are coupled to an interferometer or other device, and data about the structural integrity of the composite structure can be obtained through analysis of the scattered laser energy. Laser ultrasound has been shown to be very effective for the inspection of parts during the manufacturing process.

However, the equipment used for laser ultrasound is custom-designed and is presently a limiting factor regarding inspection speed. Previous generation lasers used were either flash-lamp pumped rod architectures, diode-pumped slab configurations, or gas lasers.

It is important to note that all of the various ultrasound generation laser architectures described here are by their nature large and heavy. Therefore, these architectures are unsuited to use in portable laser ultrasound inspection systems for any sort of in-service, remote, or in-the-field deployment. In addition, because they are so large and heavy, these architectures require substantial robotic fixturing and complex beam delivery systems even when they are deployed in factory environments, all of which greatly increases the initial overall cost of the laser ultrasound inspection system as well as the maintenance costs to keep the inspection system in operation in a production environment. These large complex structures are suited to external component inspections and cannot inspect all facets of assembled structures.

SUMMARY OF THE INVENTION

Embodiments of the present invention are directed to systems and methods that substantially address the above identified needs and other needs as well. The embodiments of the present invention are further described in the following description and claims. Advantages and features of embodiments of the present invention may become apparent from the description, accompanying drawings and claims.

Embodiments of the present invention provide an ultrasonic non-destructive evaluation (NDE) system operable to inspect target materials. This ultrasonic NDE system includes an articulated robot, an ultrasound inspection head, a processing module, and a control module. The ultrasound inspection head couples to or mounts on the articulated robot. The ultrasound inspection head is operable to deliver a generation laser beam, a detection laser beam, and collect phase modulated light scattered by the target materials. The processing module processes the phase modulated light and produces information about the internal structure of the target materials. The control module directs the articulated robot to position the ultrasound inspection head according to a determined scan plan.

Laser ultrasonic inspection has been demonstrated as a cost-effective tool for the inspection of polymer-matrix composites. As the use of composites increases in different industries and in more complex structures, the present invention provides the ability for in-service inspection of integrated components. The embodiments of the present invention place a laser ultrasonic sensor or ultrasonic inspection head at the end of the articulated robot. This is made possible by improved laser sources and/or the use of remote laser sources which may be fiber-coupled to laser beam delivery heads for both the generation and detection laser beams within the ultrasound inspection head. This provides a significant advantage in that articulated robots may be used to inspect areas within assembled structures previously inaccessible to gantry robots.

Yet another environment of the present invention provides a robotic composite inspection system operable to generate ultrasonic surface displacements on a surface of a remote target. This large area composite inspection system may be part of a large industrial robotic gantry based inspection system or use diode pumped fiber lasers to produce generation and/or detection laser beams and in so doing allow more compact robots and inspection systems to be built.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGURES, like numerals being used to refer to like and corresponding parts of the various drawings.

Laser-ultrasonic inspection has been demonstrated as a cost effective tool for the non-destructive evaluation (NDE) of polymer-matrix composites. As these composites are increasingly used in different industries, the quantity and complexity of composite parts are increasing. Also, the installed base of composites is increasing as well. As the size and complexity of objects fabricated from composites increase, it becomes more and more difficult to position the laser-ultrasonic sensors relative to the surface to be inspected. Embodiments of the invention disclosed here propose a solution to this problem.

One embodiment places the laser-ultrasonic sensor at the end of an articulated robot (i.e. laser ultrasonic head). Laser-ultrasonic inspections are usually carried out by moving the laser ultrasonic sensor using a gantry positioning system that moves along a Cartesian (X-Y-Z) system.

Articulated robots have been used in several industries. Articulated robots provide several advantages when compared to gantry systems if the size and weight of the laser ultrasound head can be reduced. Also articulated robots offer more flexibility in the deployment. Articulated robots can be installed and displaced more easily than gantry systems. Furthermore articulated robots offer position registration not available with many mobile (i.e. cart based) systems. Articulated robots impose fewer constraints than gantry systems relatively to the room size and facility requirements. Articulated robots also offer the ability to position the laser-ultrasonic sensor within complex or assembled parts.

Figure 1:
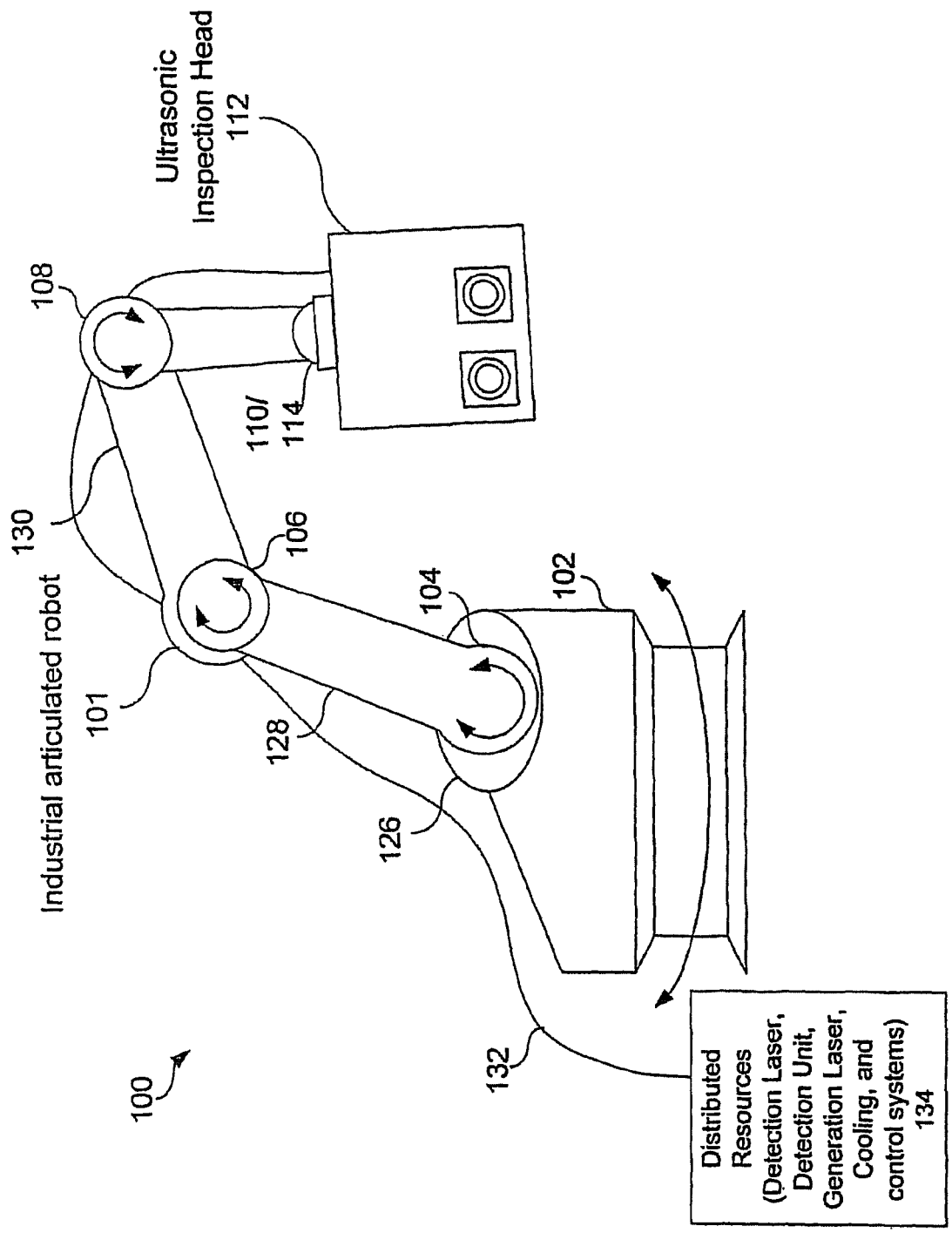
FIG. 1 depicts an articulated robot used to position an ultrasound inspection head relative to target materials in accordance with an embodiment of the present invention.

Robotic technology provides a low risk approach to automation compared to dedicated special purpose equipment. As is shown in FIG. 1, an articulated Robot 101 is provided in an ultrasonic non-destructive evaluation (NDE) system 100. System 100 includes the articulated robot 101, distributed resources 134 and ultrasound inspection head 112. Articulated robot 101 as shown in this embodiment may use a number of joints (i.e. rotary joints) to provide a number of independent motions (to support a number of degrees of freedom) in which the end effector or manipulator can be repositioned. Typically, industrial articulated robots have six degrees of freedom but might have more or less in some circumstances. Articulated robot 101 includes a platform mount 102, a first rotary joint 104, second rotary joint 106, third rotary joint 108, a fourth rotary joint 110, and end effector or manipulator 114, shoulder 126, a first arm 128, and second arm 130. Joints 104, 106, 108 and 110 may be arranged in a "chain" so that one joint supports another further in the chain. Ultrasound inspection head 112 is coupled to articulated robot 101 with the manipulator or end detector 124. Additionally the ultrasound inspection head 112 may be coupled to distributed resources 134 through various cables 132. Distributed resources 134 can be completely located on the ground, as illustrated in FIG. 1, or can be distributed at different locations on the robot. For example, not illustrated here, resources for the generation laser could be located on the ground and some other resources of the generation laser could be located on one arm of the robot like arm 128 or 130, or both. Final delivery optics for the generation laser would still be located in the ultrasound inspection head 112. Ultrasound inspection head 112 may deliver a generation laser beam and detection laser beam such as those discussed with reference to FIGS. 2 and 3 to target materials. FIG. 1 shows the articulated robot in an upward orientation on the ground. In a similar embodiment not illustrated here, the robot would be attached to the ceiling in a downward orientation. The robot could also be attached to a gantry robot, giving the maximum flexibility for positioning the robot. In that embodiment, not illustrated here, the distributed resources 134 could be located on any section of the articulated robot, on any section of the gantry robot, or on the ground.

Figure 2:
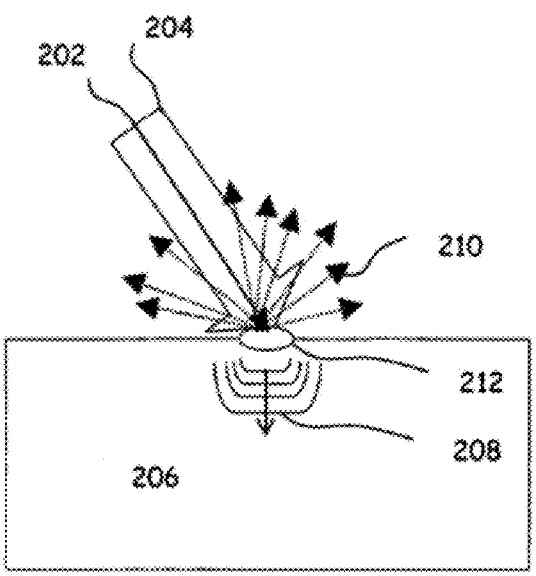
FIG. 2 illustrates the use of generation laser beam and a detection laser beam to generate and detect laser ultrasonic displacements in accordance with an embodiment of the present invention.

FIG. 2 depicts two incoming laser beams that generate and detect laser ultrasonic displacements as provided by embodiments of the present invention. Laser beam 202 generates ultrasound while illumination (detection) laser beam 204 detects the ultrasound at a remote target 206, such as a composite material under test. As shown, these lasers may be coaxially applied to remote target 206. Generation laser beam 202 causes thermo-elastic expansion 212 in target 206 that results in the formation of ultrasonic deformations or waves 208. Deformations or ultrasonic waves 208 propagate in target 206 and modulate, scatter and reflect illumination laser beam 204 to produce phase-modulated light 210 directed away from target 206 which is collected and processed to obtain information describing the internal structure of remote target 206. For purposes of this disclosure phase modulation also includes frequency modulation. The time derivative of a phase modulation corresponds to the frequency modulation. Since the term modulation in the present context means variation as a function of time, any phase modulation corresponds to a frequency modulation.

Figure 3:
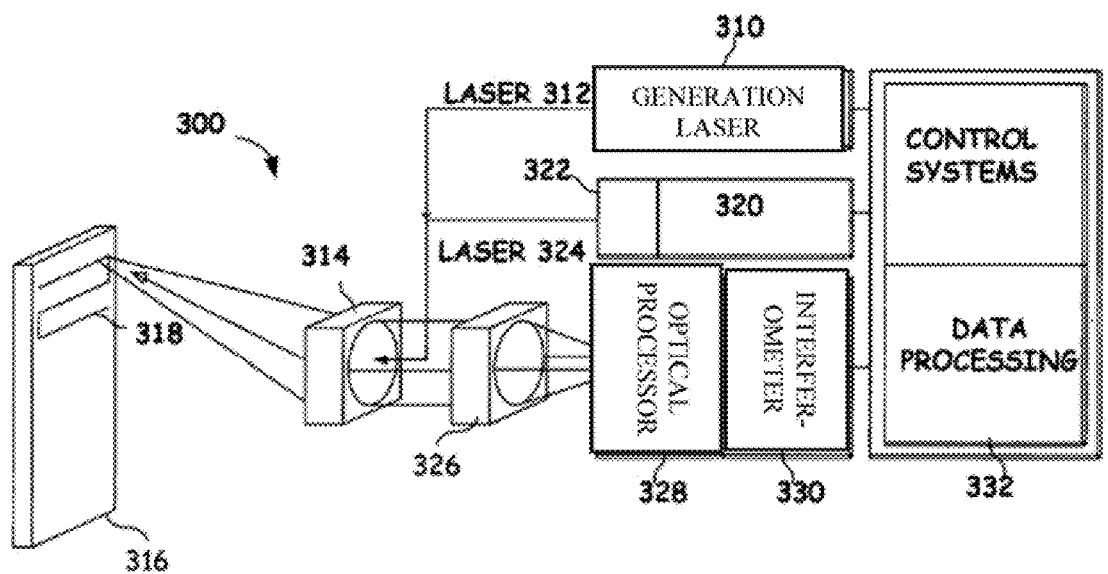
FIG. 3 provides a block diagram to show the basic components of laser ultrasound system.

FIG. 3 provides a block diagram with the basic components for performing ultrasonic laser testing. Generation laser 310 produces generation laser beam 312 which optical assembly 314 directs to target 316. As shown, optical assembly 314 includes a scanner or other like mechanism that moves laser beam 312 along a scan or test plan 318. Optical assembly 314 may include visual cameras, depth cameras, range detectors, narrowband cameras or other like optical sensors known to those having skill in the art. These optical sensors each may require calibrations prior to performing an inspection. This calibration verifies the ability of the system to integrate information gathered by various sensors. Generation laser 310 produces an ultrasonic wave 208 within target 316.

Ultrasonic wave 208 is the result of thermo-elastic expansion 212 of the composite material as the composite material absorbs the generation laser beam. Composite materials readily absorbs generation laser beam 312 without ablating or breaking down. Higher powered generation lasers are not necessarily preferred to overcome signal-to-noise ratio (SNR) issues as these can result in ablation of material at the surface of the workpiece, potentially damaging the component. In other embodiments, depending on the material being tested, some ablation may be acceptable in order to increase the SNR of the detected signal. Generation laser beam 312 has appropriate pulse duration, power, and frequency to induce ultrasonic surface deformations. For example, a transverse-excited atmospheric (TEA) $CO_2$ laser can produce a 10.6 micron wavelength beam for a 100 nanosecond pulse width. The power of the laser must be sufficient to deliver, for example, a 0.25 joule pulse to the target, which may require a 100 watt laser operating at a 400 Hz pulse repetition rate. Generation laser beam 312 is absorbed as heat into the target surface thereby causing thermo-elastic expansion without ablation.

Illumination or detection laser 320 operating in pulsed mode or CW mode does not induce ultrasonic displacements. For example, an Nd:YAG laser can be used. The power of this laser must be sufficient to deliver, for example, a 100 millijoule, 100 micro-second pulse, which may require a one kilo-watt (KW) laser. Illumination (detection) laser 320 generates detection laser beam 322. Illumination laser 320 includes or optically couples to filtering mechanism 324 to remove noise from detection laser beam 324. Optical assembly 314 directs illumination laser beam 324 to the surface of composite material 316 which scatters and/or reflects detection laser beam 324. Resultant phase modulated light is collected by collection optics 326. As shown here, scattered and/or reflected detection laser light travels back through optical assembly 314. Optional optical processor 328 and interferometer 330 process the phase modulated light to produce a signal containing information representative of the ultrasonic displacements at the surface of composite material 316. Data processing and control system 332 coordinates operation of the laser ultrasound system components. Data processing and control system 332 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 332 executes, operational instructions corresponding to at least some of the steps and/or functions as will be illustrated.

The ultrasound inspection head 112 of FIG. 1 may collect phase modulated light scattered by the target materials. Depending on the capabilities of the ultrasound inspection head, the ultrasound inspection head may include a processing module operable to process the collective phase modulated light and produce information about the internal structure of the target materials. Alternatively the generation of laser beams and processing of detected optical signals may be handled with distributed resources 114. Distributed resources 114 may include a generation laser source 316, a detection unit 318, generation laser source 322 and processing and control module 320.

Embodiments of the present invention may utilize fiber lasers within the ultrasound NDE system. Fiber laser technology may be combined with and applied to the generation and detection laser. A fiber laser detection laser is disclosed in U.S. patent application Ser. No. 11/458,377, entitled "FIBER LASER FOR ULTRASONIC TESTING" filed on Jul. 18, 2006 which is incorporated by reference in its entity for all purposes. A fiber-laser-based generation laser is disclosed in U.S. patent application Ser. No. 11/524,046, entitled "FIBER-BASED MID-INFRARED GENERATION LASER FOR LASER ULTRASOUND" filed on Sep. 9, 2006 which is incorporated by reference in its entity for all purposes The primary task of a "first" detection laser is to illuminate the spot where a "second" laser is used to generate ultrasound in the part under test. The scattered light from the first laser is collected and analyzed with an interferometer to demodulate the surface vibrations caused by the return echoes of the ultrasound at the surface of the part. The detection laser (first laser) and generation laser (second laser) may use diode pumped fiber lasers to produce a high power output.

Gas lasers able to reliably operate at repetition rates above 1000 Hz would be very heavy and bulky. Another limitation of the gas lasers is the requirement of maintenance every one to three billion shots to change parts and to clean the optics.

An all-fiber pump laser scheme may be employed by the present invention and use many small continuous wave (CW) diode lasers ('pump diodes') to pump the doped active laser fiber. This has several advantages. First of all, these low power diodes offer the very high reliability required for telecom applications and have mean time between failure (MTBF) ratings of 100,000 hours. Also, all of the fiber-coupled pump diodes are relatively small in power (typically only a few watts) and the failure of any one would have little impact on the total performance of the fiber laser. Furthermore reduced weight would reduce mechanical requirements of the articulated robot and or could be partially positioned within the distributed resources.

Thermal management of a fiber laser/amplifier is more easily handled than within a traditional bulk crystal gain medium. Heat removal from the fiber-coupled pump diodes is managed separately from the gain medium (the doped active laser fiber), and the ratio of the fiber surface area (where heat is extracted) to the volume is many orders-of-magnitude larger than the surface-to-volume ratio for a rod or slab laser architecture. As a result, a fiber laser can be operated in a fundamental (TEM00) transverse mode with very little wavefront distortion ($M^2<1.2$). Fiber lasers do not use traditional discrete or bulk optics such as mirrors or lenses. Therefore contamination issues within the laser cavity are eliminated. This is particularly advantageous for industrial inspection systems that run around the clock in production applications. A fiber laser looks like a piece of industrial electronics. Flexible architecture enables mobile and possibly portable laser ultrasonic inspection equipment designs. Overall, fiber lasers are well suited for harsh industrial environments.

Figure 4:
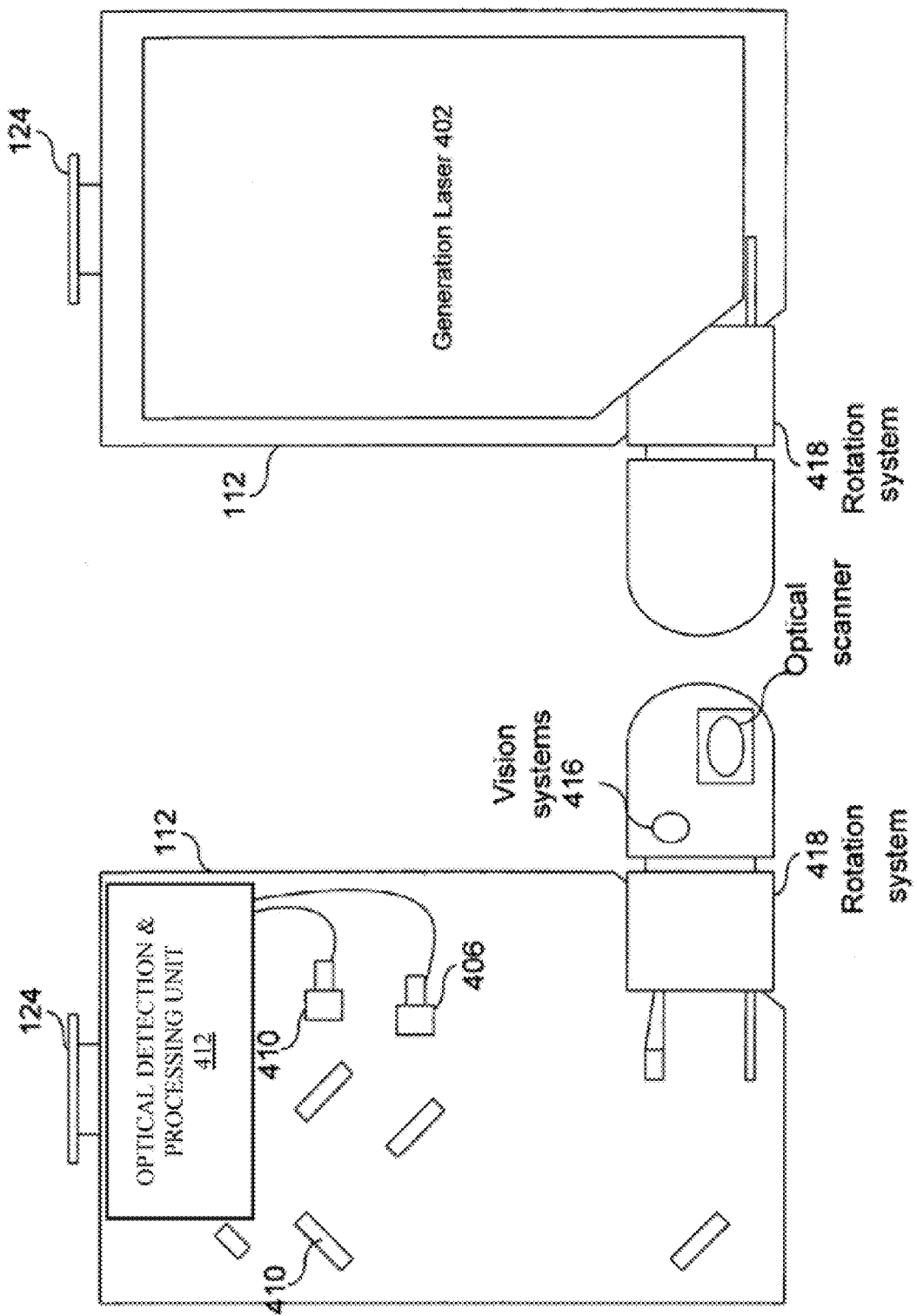
FIG. 4 provides a functional diagram of one embodiment of an ultrasound inspection head in accordance with embodiments of the present invention.
Figure 5:
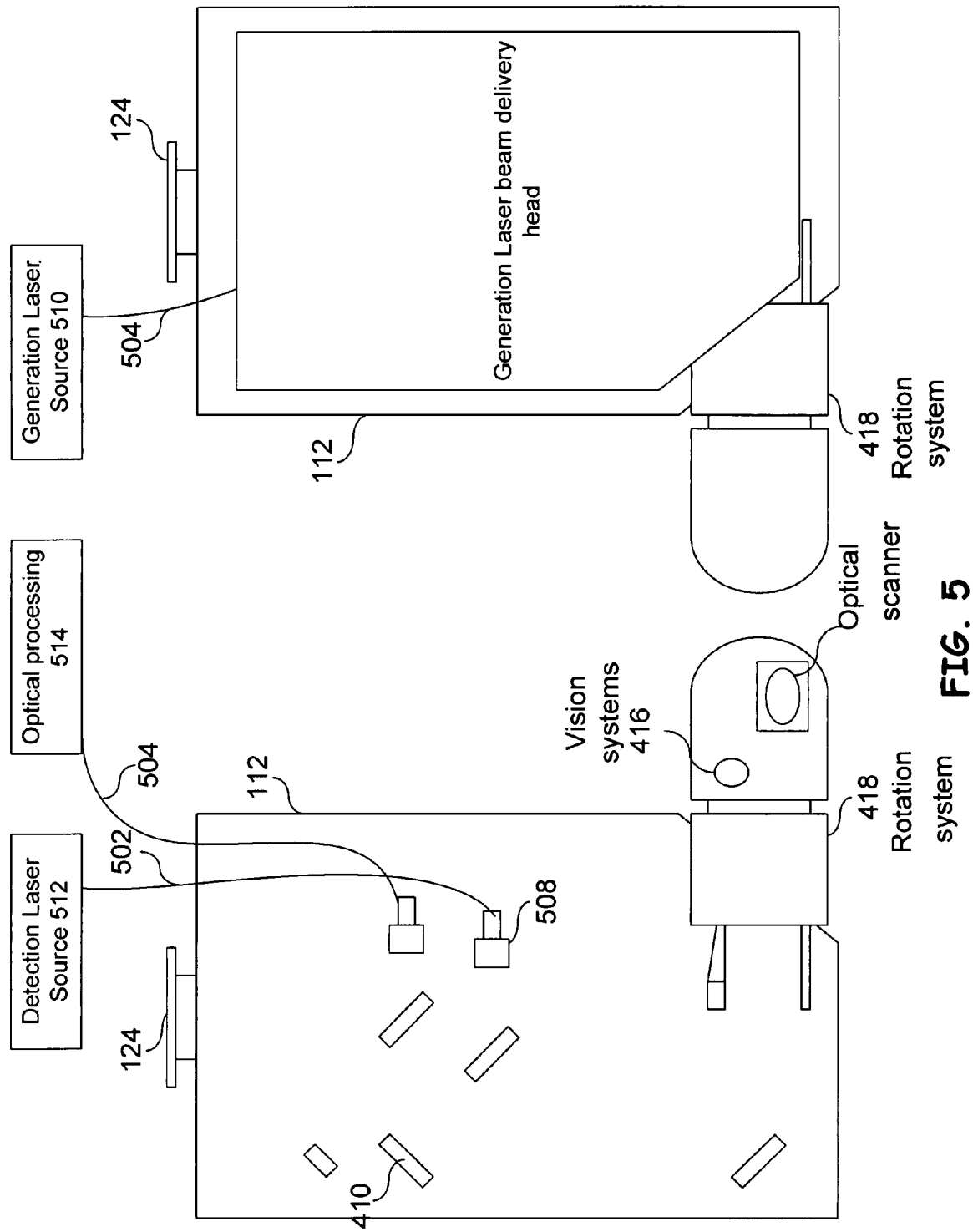
FIG. 5 provides a functional diagram of one embodiment of an ultrasound inspection head that utilizes distributed resources in accordance with embodiments of the present invention.

FIG. 4 provides a functional diagram of one embodiment of an ultrasound inspection head 112 in accordance with embodiments of the present invention. In one embodiment generation lasers 402 may be provided to produce generation laser beam 202 which is then directed to the target materials. Similarly a detection laser 406 may be used to produce a detection laser beam 204 also directed to the target materials. Collection optics 410 may be used to collect phase modulated light scattered by the remote target. This phase modulated light is then processed using an optical detection and processing unit 412. Vision system 416 and its associated processors may then determine the position and orientation of the target materials relative to the ultrasound inspection head. FIG. 5 shows a rotation system 418 that might facilitate the positioning of the optical scanner relatively to the part to be inspected. To reduce the size of the ultrasound inspection head, the rotation system 418 can be absent from the ultrasonic inspection head (not illustrated here). In this latter embodiment, the positioning of the ultrasonic head to inspect a part is entirely completed by the various degrees of freedom of the articulated robot. Due to weight concerns and economic concerns some of these modules (such as the laser sources) associated with the generation laser, detection laser, and required processing moved from the ultrasound inspection head in order to reduce the weight of the ultrasound inspection head and the mechanical requirements of the articulated robot.

Such an embodiment is shown in FIG. 5 where optical fibers 502, 504 and 506 may be used to couple the detection laser source and generation laser source to the detection laser head 508, generation laser head 510, and optical processor 514 respectively. Here the generation laser source and detection laser source 512 are remotely located as part of distributed resources as shown in FIG. 4. Optical fiber 504 may be used to provide collected phase modulated light to an optical processing system 514 within the detection unit 128 of FIG. 1. Removing these resources from the ultrasound inspection head reduces the overall size and weight requirements of the articulated robot. This potentially results in not only lower costs but increased flexibility and capability of the robot. The detection laser source 512 and generation laser source 510 can be distributed on various arms of the robot or completely off the robot.

Figure 6:
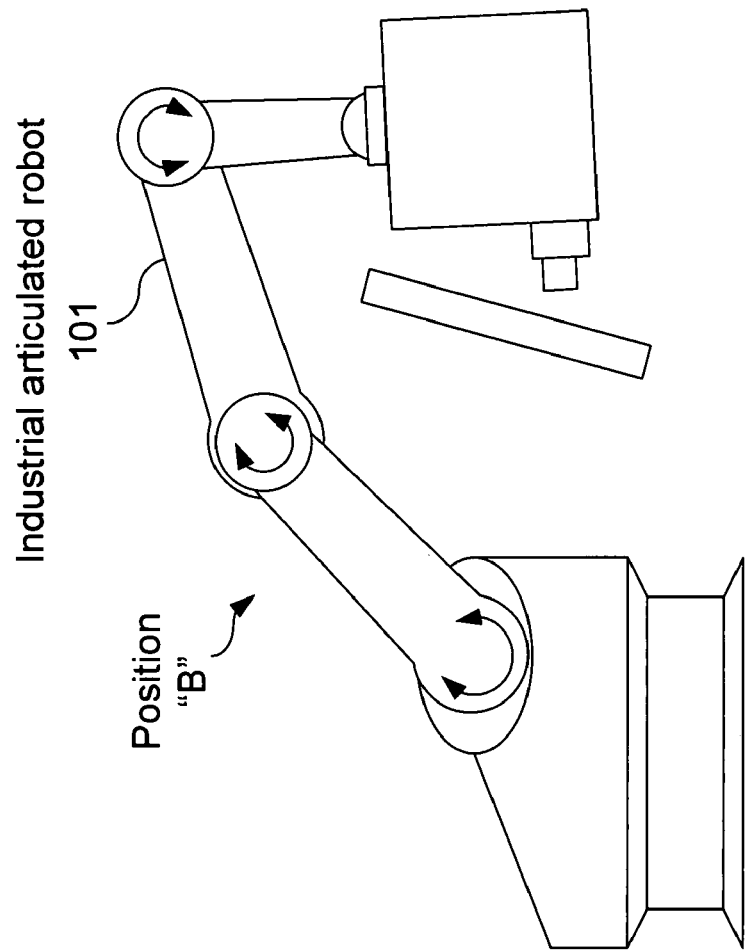
FIG. 6 depicts the articulated robot articulated in multiple positions that facilitate NDE of materials in accordance with embodiments of the present invention.
Figure 6:
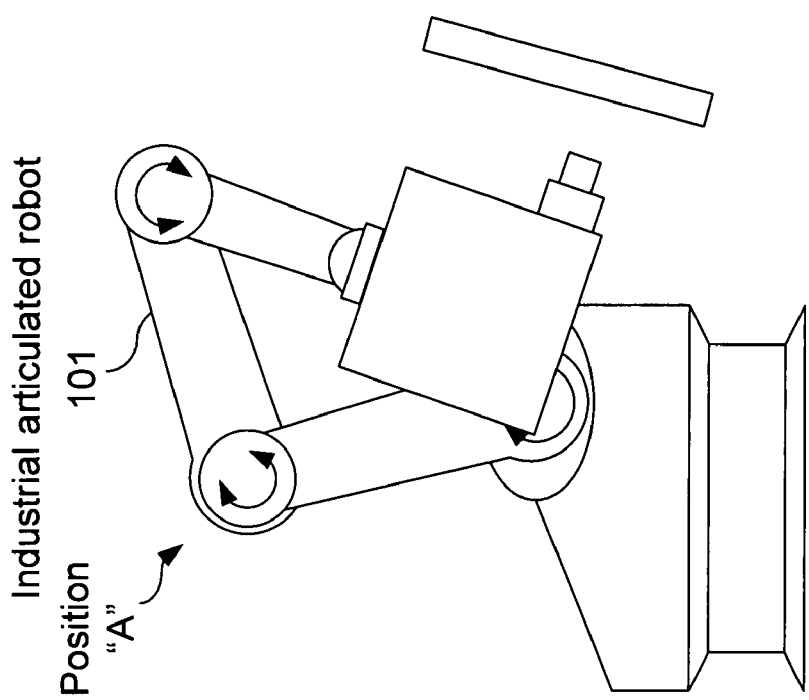

FIG. 6 depicts the articulated robot 101 articulated in position "A" and position "B". These different positions of the robot allow the laser ultrasound head 112 to be placed in different positions while attempt to the target materials in order to completely cover and fully inspect the target materials.

Figure 7:
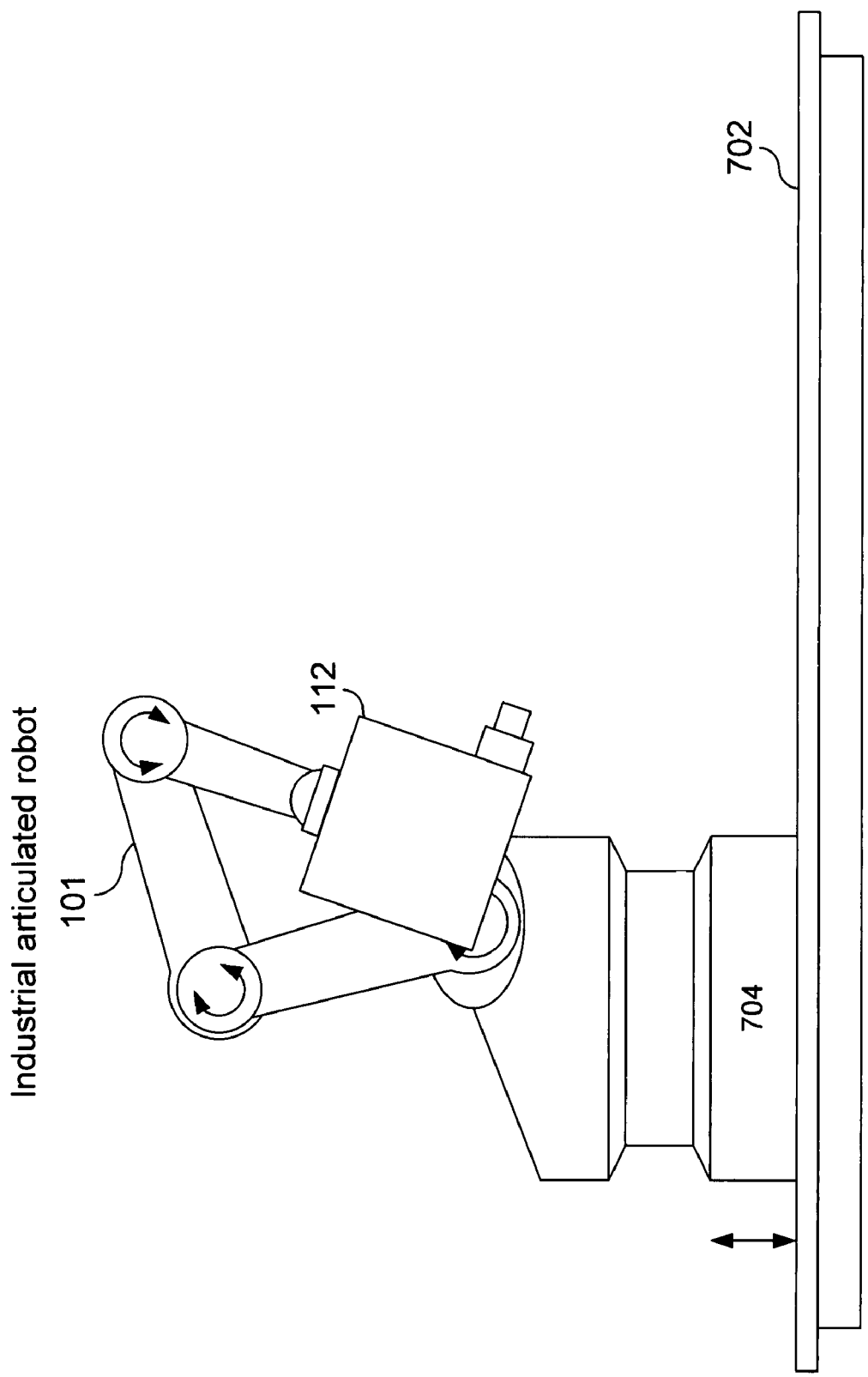
FIG. 7 shows an articulated robot mounted on a rail where the rail allows for controlled movement of the articulated robot and laser ultrasound head within a predetermined work envelope n accordance with embodiments of the present invention.

FIG. 7 shows that articulated robot 101 may be mounted on a rail 702 where rail 702 allows for controlled movement of the articulated robot and laser ultrasound head 112 within a predetermined work envelope. The work envelope defines the boundaries within which the articulated robot 101 can reach to position a laser ultrasound head 112. Rail 702 is not necessarily straight and can take a semi-circular, circular, or any shape necessary to fit the required work envelope. Additionally platform 704 may translate along a Z axis in order to help elevate or lower laser ultrasound head 112 in order to fully reach and inspect the target materials. Platform 704 can be present even in the case where the rail 702 would not be present.

In a similar embodiment not illustrated here, the articulated robot could be on a rail system that would move the articulated in two dimensions (X-Y). The platform 704 might or might not be present to provide additional positioning capabilities in the Z direction. In another similar embodiment not illustrated here, the rail system and platform 704 could be replaced by a gantry robot, and the articulated robot would be attached in a downward orientation to this gantry robot that would provide the additional positioning capabilities in three dimensions (X-Y-Z).

Figure 8:
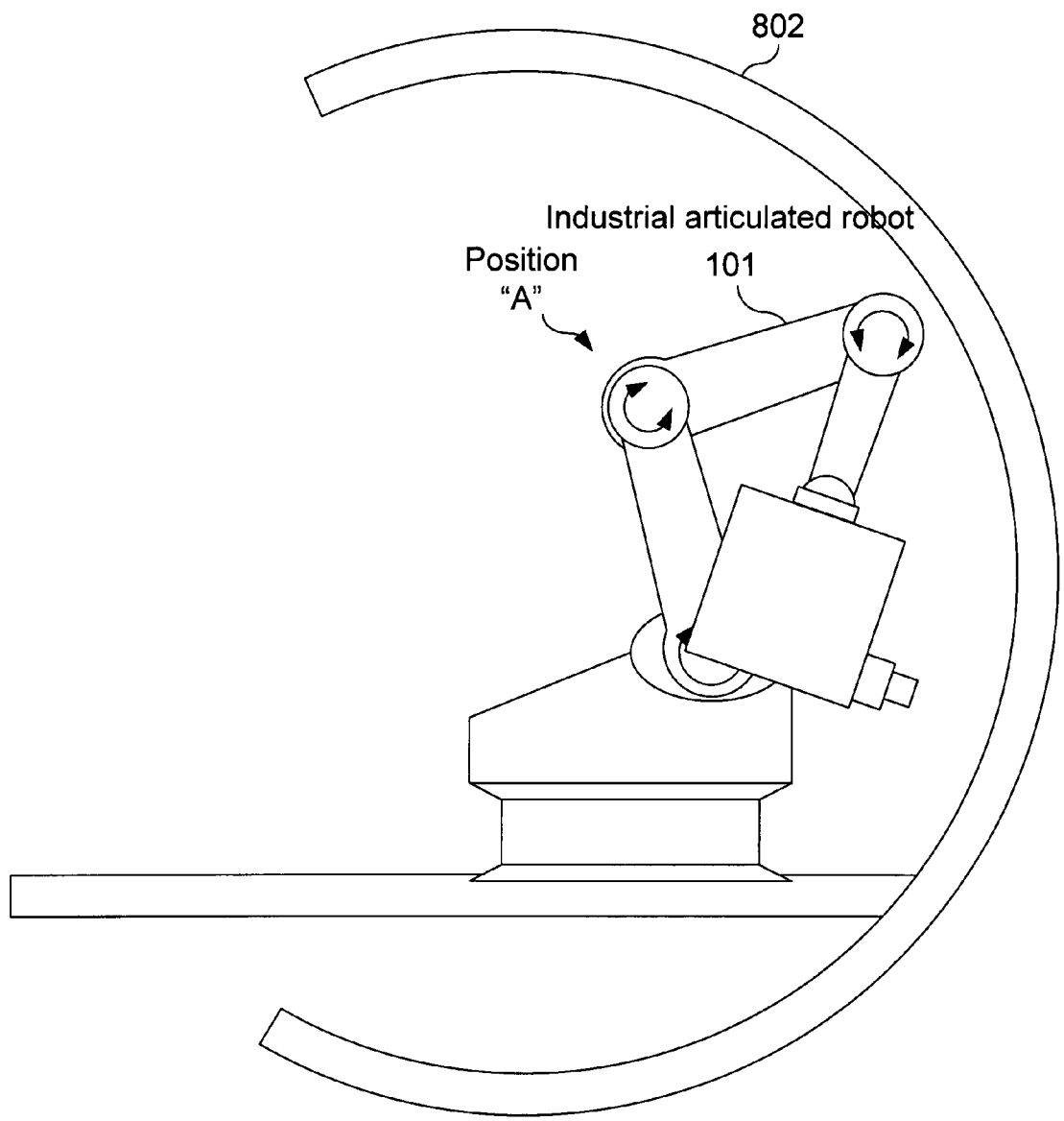
FIG. 8 shows an articulated robot articulated within an assembled structure such as an aircraft fuselage where the articulation allows for controlled movement of the articulated robot and laser ultrasound head within a confined space in accordance with embodiments of the present invention.

An important advantage is illustrated in FIG. 8. FIG. 8 depicts an articulated robot 101 having ultrasound inspection head 112 that may be positioned within a completed or integrated structure that contains internal surfaces to be inspected. FIG. 8 depicts that the articulated robot may either fully or partially enter a completed structure 802 such as an aircraft fuselage. This aircraft fuselage may be made of individual components fabricated from composite materials that require inspection. Thus not only the fabrication of the part may be inspected, but also the completed structure. This allows the inspection process to identify potential problems during assembly or once the structure is in service.

Robot 101 may be mounted on a rail 702 in order to facilitate the movement of the ultrasound inspection head 312 without requiring motion of the completed structure 802. The work envelope associated with the articulated robot may define boundaries such that the articulated robot may fully inspect but not collide with integrated structure 802. The vision system discussed with reference to FIGS. 4 and 5 or other like position detection systems (i.e. laser-based, radar-based or acoustic-based) may be used to prevent collisions and to determine the orientation and position of the target materials (including assembled structures) relative to the ultrasound laser head and articulated robot.

Figure 9:
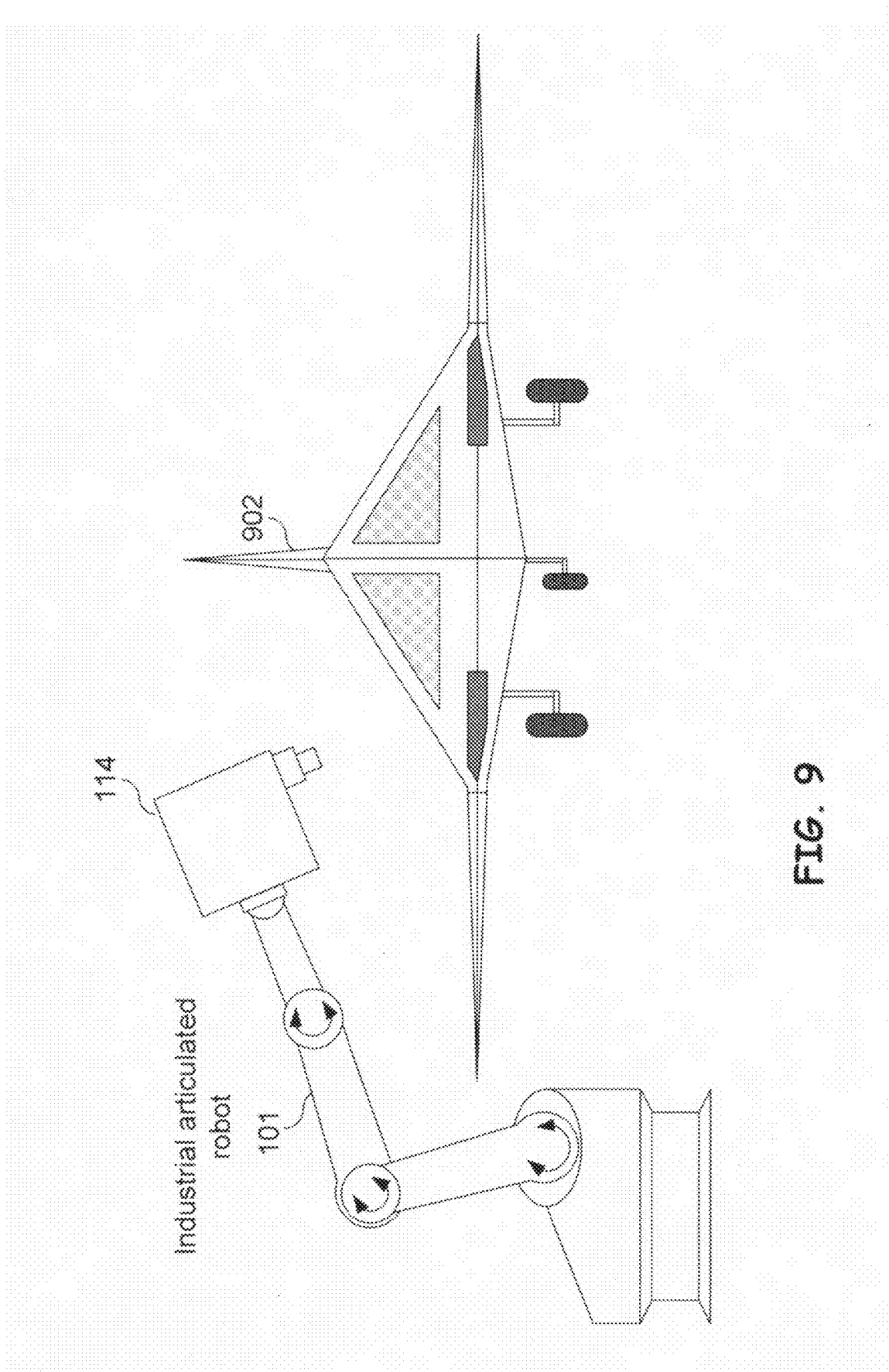
FIG. 9 depicts an in service application of the ultrasound NDE system provided by embodiments of the present invention.

FIG. 9 depicts an in-service application of the ultrasound NDE system provided by embodiments of the present invention. In this embodiment articulated robot 101 and laser ultrasound inspection head 112 may be mounted in a service location such as a hanger in order to facilitate the inspection of integrated structures, such as but not limited to aircraft 902. Aircraft 902 may have many components constructed or fabricated from composite materials where in service inspection allows the structural integrity of the composite materials to be evaluated without requiring disassembly of the aircraft.

Figure 10:
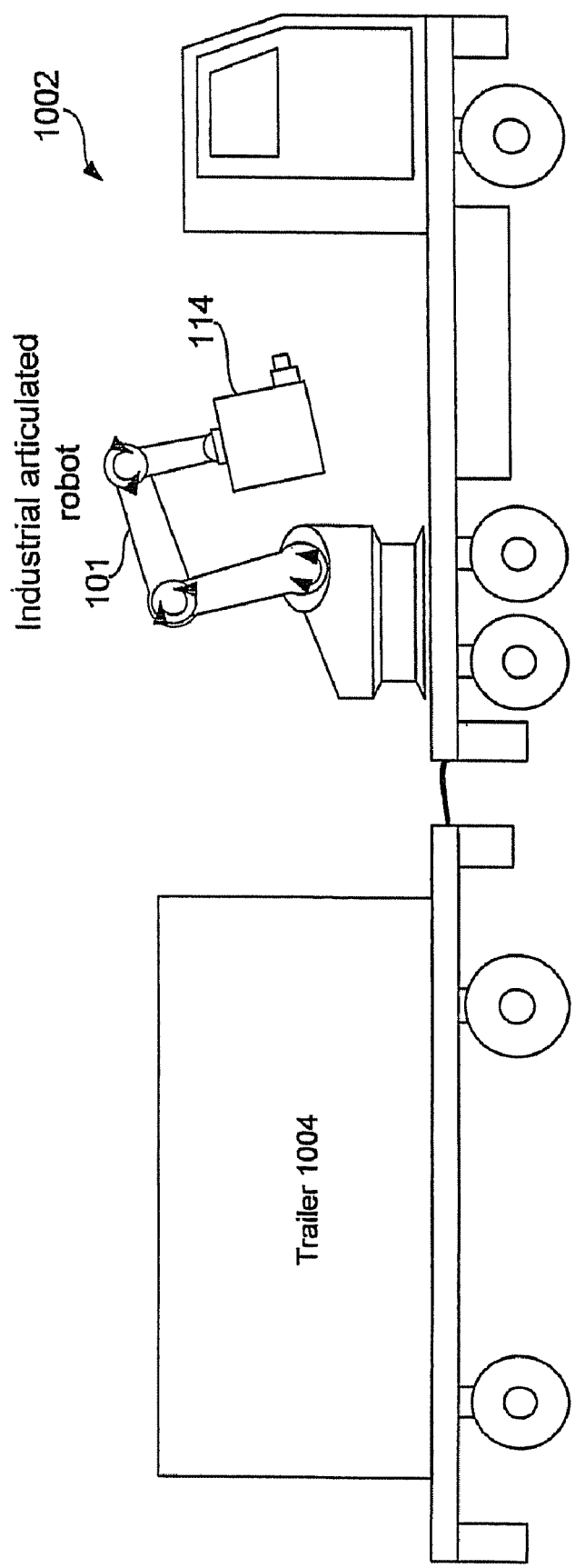
FIG. 10 depicts a mobile application of the ultrasound NDE system provided by embodiments of the present invention.

FIG. 10 depicts another in-service application wherein the articulated robot 101 may be mounted to a mobile platform 1002. Trailer 1004 couples to mobile platform 1002. Trailer 1004 may house distributed resources required by the NDE system. In this instance the ultrasound NDE system may be brought to an integrated structure to be inspected. This differs from FIG. 9 where an in-service system used to inspect an integrated system which brought to the inspection system. Either embodiment provides increased flexibility in performing in-service inspections. In addition, the embodiment illustrated by FIG. 10 can present several advantages for the ultrasonic inspection of composite parts in a manufacturing environment. For example, part handling can be minimized by bringing the inspection system to the manufactured part especially when that part is very large, like a composite fuselage. Minimizing part handling decreases the possibilities of damaging the part during manufacturing. An additional advantage of the mobile platform 1002 in a manufacturing environment is that the inspection system can be moved out of the way when required. Finally, the inspection resources can be moved at different locations in the plant as required by modifications to the production line.

Locating the pump laser head meters away from generation laser beam delivery head allows a compact mid-IR generation laser head since the overall payload and the stability requirements for robotic systems used to deliver the generation laser beam are significantly relaxed. Only a compact and lightweight module containing the generation laser beam delivery head, detection laser beam delivery head and collection optics is required to be mounted within the inspection head of the robotic system. This allows the deployment of a mid-IR laser source using smaller articulated robots. Thus, new composite inspection opportunities are created for in-service composite NDE using portable laser ultrasound systems.

In operation the present invention allows laser ultrasonic test equipment to be used in a wider range of environments while testing more complex surfaces or surfaces within limited access areas. The embodiments of the present invention may utilize fiber lasers or distributed resources to generate and deliver detection and generation laser beams to target materials to be tested. Doing so allows the overall size of a laser ultrasound based NDE system to be greatly reduced. For example, instead of a large gantry robotic based system, a much smaller articulated robotic system may be used to deliver generation and detection laser beams to, and collect phase modulated light from the surface of the target to be tested.

This allows the laser ultrasound inspection system offered by embodiments of the present invention to be used to not only inspect individual components but to assess the internal structure of integrated components. Thus, not only can individual parts be inspected by the laser ultrasound system offered by embodiments of the present invention but assembled structures made from individual parts may be inspected. This allows inspections to be made after the integrated structure has been built to determine if changes in the internal structure over the life of the structure have occurred. Additionally, embodiments of the present invention may provide an entirely mobile system that uses fiber lasers to generate and detect ultrasonic displacements at a remote target in the field without the problems often associated with free space delivery of generation and detection laser beam(s).

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. An ultrasonic non-destructive evaluation (NDE) system operable to inspect target materials, the system comprising:

an articulated robot having an arm with a series of arm members connected to each other by rotary joints, the robot being operably mounted on a platform;

an ultrasound inspection head coupled to a distal one of the arm members;

collection optics mounted on the inspection head;

a fiber-laser-based generation laser source remotely located from the inspection head;

a generation laser head mounted on the inspection head and coupled to the generation laser source by an optical fiber for directing a generation laser beam selectively to the target materials from the ultrasound inspection head, so that when the generation laser beam contacts the target materials, ultrasonic displacements are formed thereon, the optical fiber for the generation laser beam extending through at least some of the joints;

a fiber-laser-based detection laser source remotely located from the inspection head;

a detection laser head mounted on the inspection head and coupled to the detection laser source by an optical fiber for directing a detection laser beam selectively to the target materials, so that when the detection laser beam contacts the ultrasonic displacements formed on the target materials, the detection laser beam is scattered to produce phase modulated light that is reflected to the collection optics, the optical fiber for the detection laser beam extending through at least some of the joints; and a processing module remotely located from the inspection head and coupled to the collection optics by an optical fiber, the processing module being operable to process the phase modulated light and produce information about the internal structure of the target materials, the optical fiber for the processing module extending through at least some of the joints; and a control module operable to direct the arms to position the ultrasound inspection head adjacent but spaced from the target materials according to a scan plan.

2. The ultrasonic NDE system of claim 1, wherein inspection head is connected to said distal one of the arm members by an additional rotary joint, and the inspection head is moveable with respect to the platform by up to six degrees of freedom.

3. The ultrasonic NDE system of claim 1, wherein the platform translates along a rail relative to the target materials.

4. The ultrasonic NDE system of claim 1, wherein the platform comprise a vehicle operable to reposition the platform relative to the target materials.

5. The ultrasonic NDE system of claim 1, wherein the generation laser source, the detection laser source and the processing module are located remote from the arm members.

6. The ultrasonic NDE system of claim 1, further comprising a distributed resources unit containing the generation laser source, the detection laser source and the processing module, wherein the distributed resources and the platform are contained within a mobile transport system.

7. The ultrasonic NDE system of claim 1, wherein the articulated robot is operable to position the ultrasound inspection head within an aircraft fuselage.

8. The ultrasonic NDE system of claim 1, wherein the control module comprises a vision system operable to determine a position and orientation of the target materials relative to the ultrasound inspection head.

9. An ultrasonic non-destructive evaluation (NDE) system for use in inspecting composite target materials, the system comprising:

an articulated robot comprising:
  a platform mount;
  a first arm member having a proximal end connected to the platform mount by a first rotary joint and moveable about the platform mount by a number of degrees of freedom;
  a second arm member having a proximal end attached to a distal end of the first arm member by a second rotary joint;
  a third arm member having a proximal end attached to a distal end of the second arm member by a third rotary joint;;
an ultrasound inspection head coupled to a distal end of the third arm member by a fourth rotary joint;
a generation laser head mounted in the inspection head
a fiber-laser-based generation laser source remotely located from the ultrasound inspection head and the arm members and coupled to the generation laser head by an optical fiber, the optical fiber extending into and out of the second and third rotary joints;
a detection laser head mounted in the inspection head;
a fiber-laser-based detection laser source remotely located from the ultrasound inspection head and the arm members and coupled to the detection laser head by an optical fiber, the optical fiber for the detection laser source extending into and out of the second and third rotary joints;
collection optics in the ultrasound inspection head;
a processing module remotely located from the ultrasound inspection head and the arm members and coupled to the collection optics by an optical fiber, the optical fiber for the collection optics extending into and out of the second and third rotary joints; and a control module remotely located from the ultrasound inspection head and the arm members for controlling movement of the arm members so as to position the ultrasound inspection head adjacent to the composite target materials.

10. The ultrasonic NDE system of claim 9, wherein the platform mount is set on a surface and the generation laser and detection laser are on the surface.

11. The ultrasonic NDE system of claim 9, further comprising a position measuring system mounted to the inspection head and operable to determine the position and orientation of the target materials relative to the ultrasound inspection head.

12. The ultrasonic NDE system of claim 9 wherein the detection laser comprises:
  a master oscillator operable to generate a seed laser beam; and
  at least one diode pumped laser amplifier operable to amplify the seed laser beam,
  wherein at least the master oscillator or the at least one diode pumped laser amplifier comprises diode pumped fiber and wherein the master oscillator or the at least one diode pumped laser amplifier of the detection laser comprises a diode pumped slab laser.

13. The ultrasonic NDE system of claim 9 wherein the generation laser includes a laser beam pumping at least one optical parametric oscillator with or without optical parametric amplifiers.

14. A method of conducting an ultrasonic non-destructive evaluation (NDE) on composite target materials comprising:
  a) providing a robot having a series of arm members connected together by rotary joints and coupled on a proximal end to a platform mount;
  b) mounting an ultrasonic inspection head to a distal end of the arm members by an additional rotary joint, the inspection head having a generation laser head, a detection laser head, and collection optics;
  c) mounting a laser-fiber-based generation laser source, a laser-fiber-based detection laser source, and a processing module remote from the inspection head and, by optical fibers, connecting the generation laser source to the generation laser head, the detection laser source to the detection laser head, and the processing module to the collection optics, the optical fibers extending into and out of at least some of the rotary joints;
  d) moving the distal end of the arm members and positioning the inspection head adjacent to the target materials;
  e) forming ultrasonic displacements on the target materials by directing a generation laser beam to the target materials from the generation laser source through at least one of the optical fibers and out the generation laser head;
  f) phase modulating light by directing a detection laser beam at the ultrasonic displacements from the detection laser source through at least one of the optical fibers and out the detection laser head;
  g) collecting the phase modulated light through the collection optics and delivering the collected phase modulated light through at least one of the optical fibers to the processing module; and
  h) with the processing module, processing the phase modulated light to determine information about the target.

15. The method of claim 14, further comprising after step (h), repositioning the the distal end of the arm members by independly moving at least some of the arm members relative to others of the arm members and repeating steps (e)-(h).

16. The method of claim 15, further comprising moving the distal end of the arm members in six degrees movement.

17. The method of claim 14, wherein the target materials comprise a san aircraft having a fuselage, the method further comprising transporting the entire robot into an interior of the fuselage and repeating steps (e)-(h).

* * * * *